(12) United States Patent
Yarnall et al.

(10) Patent No.: US 8,927,214 B2
(45) Date of Patent: Jan. 6, 2015

(54) METHODS AND COMPOSITIONS FOR DUAL EXTRACTION OF PROTEIN AND NUCLEIC ACID

(75) Inventors: Michele Susan Yarnall, Durham, NC (US); Wenling Wang, Durham, NC (US); Karen Moore, Durham, NC (US); Mary Fielder, Durham, NC (US)

(73) Assignee: Syngenta Participations AG, Basel (CH)

( * ) Notice: Subject to any disclaimer, the term of this patent is extended or adjusted under 35 U.S.C. 154(b) by 152 days.

(21) Appl. No.: 13/450,039

(22) Filed: Apr. 18, 2012

(65) Prior Publication Data

US 2013/0280718 A1    Oct. 24, 2013

(51) Int. Cl.
*C12Q 1/68*    (2006.01)
*C12P 19/34*    (2006.01)

(52) U.S. Cl.
USPC .......................................... 435/6.1; 435/91.2

(58) Field of Classification Search
USPC ....................................................... 435/91.2
See application file for complete search history.

(56) References Cited

U.S. PATENT DOCUMENTS

| | | |
|---|---|---|
| 6,204,375 B1 | 3/2001 | Lader |
| 2003/0131377 A1 | 7/2003 | Anderson et al. |
| 2011/0098462 A1 | 4/2011 | Ehwald et al. |
| 2011/0244468 A1 | 10/2011 | Hollander et al. |

OTHER PUBLICATIONS

Protein Buffers, Luminex Corporation website (2007) online, Retrieved on Jun. 8, 2012 from the Internet (2 pages).
Invitrogen: Guanidine Isothiocyanate Solution (2006) online, Retrieved on Jun. 8, 2012 from the Internet (4 pages).
Tolosa et al. "Column-Based Method to Simultaneously Extract DNA, RNA, and Proteins from the Same Sample" *Bio Techniques* 43:799-804 (Dec. 2007).
International Search Report and Written Opinion for International Application No. PCT/US12/34086, dated Jul. 13, 2012 (8 pages).

*Primary Examiner* — Cynthia B Wilder
(74) *Attorney, Agent, or Firm* — Myers Bigel Sibley & Sajovec, PA

(57) ABSTRACT

The present invention provides a method of isolating nucleic acid and protein from the same biological sample, comprising, in the following order: a) disrupting the biological sample; b) contacting the disrupted biological sample of (a) with a protein lysis buffer that lacks any component that denatures or reduces protein to produce a first lysate; c) centrifuging the first lysate of (b) to produce a first supernatant containing protein and a pellet containing nucleic acid; d) removing the first supernatant of (c), thereby isolating protein from the biological sample; e) contacting the pellet of (d) with nucleic acid lysis buffer to produce a second lysate; f) centrifuging the second lysate of (e) to produce a second supernatant containing nucleic acid; and g) removing the second supernatant of (f), thereby isolating nucleic acid from the same biological sample.

11 Claims, No Drawings

METHODS AND COMPOSITIONS FOR DUAL EXTRACTION OF PROTEIN AND NUCLEIC ACID

FIELD OF THE INVENTION

The invention relates to methods and compositions for extraction of protein and nucleic acid from a single tissue sample.

BACKGROUND OF THE INVENTION

Biological samples, e.g., plant tissue samples, are routinely tested for the presence of the gene (DNA) and whether the gene product (protein) is expressed. Currently, tissues from organisms, such as the plants or animals, have to be sampled separately for each of these tests. If both the protein and DNA can be extracted from the same sample, then a significant savings would be achieved in both consumable costs as well as time and labor savings. Methods exist for simultaneous extraction of DNA/RNA/protein but the resulting protein, extracted with buffers that denature the protein, is not suitable for measurement in quantitative methods such as enzyme linked immunosorbent assay (ELISA); it can only be measured by methods that can employ denatured proteins (e.g., western blot). Existing methods isolate the nucleic acid components first to prevent any potential degradation of this material, but this process will cause the denaturation of the proteins in the mixture. Thus, the present invention overcomes previous shortcoming in the art by providing compositions and methods for dual extraction of undenatured protein and nucleic acid from a single tissue sample.

SUMMARY OF THE INVENTION

The present invention provides a method of isolating nucleic acid and protein from the same biological sample, comprising, in the following order: a) disrupting the biological sample; b) contacting the disrupted biological sample of (a) with a protein lysis buffer that lacks any component that denatures or reduces protein to produce a first lysate; c) centrifuging the first lysate of (b) to produce a first supernatant containing protein and a pellet containing nucleic acid; d) removing the first supernatant of (c), thereby isolating protein from the biological sample; e) contacting the pellet of (d) with nucleic acid lysis buffer to produce a second lysate; f) centrifuging the second lysate of (e) to produce a second supernatant containing nucleic acid; and g) removing the second supernatant of (f), thereby isolating nucleic acid from the same biological sample.

These and other aspects of the invention are set forth in more detail in the description of the invention below.

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

The present invention is based on the unexpected discovery that both protein (e.g., undenatured protein) and nucleic acid of good quality for analysis can be extracted from the same biological sample. The protein that is isolated is not denatured and can be tested for functional activity or measured in other assays without dilution to remove the denaturation agents. The nucleic acid that is isolated retains its integrity through the protein isolation process, during which nucleases are present. Thus in one embodiment, the present invention provides a method of isolating nucleic acid and protein (e.g., undenatured protein or protein in its native configuration) from the same biological sample, comprising, in the following order: a) disrupting the biological sample; b) contacting the disrupted biological sample of (a) with a protein lysis buffer that lacks any component that denatures or reduces protein to produce a first lysate; c) centrifuging the first lysate of (b) to produce a first supernatant containing protein and a pellet containing nucleic acid; d) removing the first supernatant of (c), thereby isolating protein from the biological sample; e) contacting the pellet of (d) with nucleic acid lysis buffer to produce a second lysate; f) centrifuging the second lysate of (e) to produce a second supernatant containing nucleic acid; and g) removing the second supernatant of (f), thereby isolating nucleic acid from the same biological sample.

In some embodiments of the methods described herein, nonlimiting examples of ways to disrupt a biological sample include physical disruption (e.g., mortar and pestle, shearing, sonication, processors, homogenization by high pressure, filtration), freeze/thaw cycles to allow for cell lysis, permeabilization, etc., as are known in the art.

In some embodiments of the method above, the protein lysis buffer can be Protein Lysis Buffer A (phosphate buffered saline with 0.05% Tween-20) or BB-PVP-Tw buffer (borate buffer 0.1 M, pH 7.5, 0.2% polyvinylpyrrolidone (PVP), 0.5% Tween-20). The lysis buffer employed in the methods of this invention maintains the biological structure and function of the protein in the biological sample and does not denature or reduce the protein. Other biological buffers that can be used in the methods of this invention include buffers that maintain the pH of the solution in a range from about 4.5 to about 9.0 (e.g., Tris, MES, HEPES, MOPS, PIPES, Imidazole, Citrate and others as are know in the art).

In particular embodiments, the protein lysis buffer lacks any (e.g., any detectable amount) component that denatures or reduces protein. Nonlimiting examples of such components include sodium dodecyl sulfate (SDS), urea, guanidine, a buffer with a pH above about 9.0 or pH below about 4.5, 2-mercaptoethanol and dithiothreitol.

In some embodiments of the method above, the nucleic acid lysis buffer is PA lysis buffer (4 M guanidine thiocyanate, 10 mM Tris, pH 7.5), LG extraction buffer (200 mM Tris HCl, pH 8.5, EDTA 25 mM, 1% SDS), Promega Lysis Buffer A, or CTAB buffer (2% CTAB, 100 mM Tris HCl, pH 8.0, 20 mM EDTA, 1.4 M NaCl, 40 mM 2-mercaptoethanol), NaOH and SDS or Tween.

In various embodiments, the isolation method above can further comprise the step of detecting and/or quantitating protein in the supernatant (e.g., the first supernatant) by any method known for detecting and/or quantitating protein. Nonlimiting examples of such methods include ELISA, BCA, Bradford assay, western blot, immunoprecipitation, immunoassay, chromatographic methods such as HPLC, enzymatic methods, functional assays and any other method known to detect/quantitate protein.

In some embodiments, the method described above can further comprise the step of analyzing (e.g., detecting and/or quantitating) the nucleic acid (e.g., the nucleic acid in the second supernatant) by any method available to detect and/or quantitate nucleic acid (e.g., DNA, RNA or both) in a sample. Nonlimiting examples of such methods include electrophoresis, amplification reactions such as the polymerase chain reaction (PCR), realtime PCR, TaqMan assays, etc., as are known in the art.

In the methods of this invention, the extracts of this invention can be prepared as described herein and can be stored at about 4° C. (e.g., about 2° C., 3° C., 4° C., 5° C., 6° C., etc.) with or without the PBST removed for up to about 24 hrs (e.g., 12, 13, 14, 15, 16, 17, 18, 19, 20, 21, 22, 23, 24, 25, 26, 27, 28, 29, 30, 31, 32, 33, 34, 35, 36 hrs, etc.) without loss (e.g., a detectable loss or measurable loss of less than about 50%, 40%, 30%, 20%, 10%, 5%, 2%, 1% or 0% according to the assays described herein) of protein and/or without degradation (e.g., a detectable or measurable degradation of less than about 50%, 40%, 30%, 20%, 10%, 5%, 2%, 1% or 0% according to the assays described herein) of DNA.

In some embodiments of this invention, the biological sample can be from a plant. Nonlimiting examples of biological sample sources from plant include leaf tissue, seed tissue, root tissue, stem tissue, flower tissue, etc.

The methods of this invention can also be employed to isolate protein (e.g., non-denatured and non-reduced protein) and nucleic acid from a biological sample from an animal. Sources of animal biological samples, such as blood and blood components, body fluids, tissues, etc., are well known in the art.

The plant of this invention can be any plant from which a tissue sample can be obtained for use in the methods described herein. Nonlimiting examples include field crops such as maize, soy, sugarcane, sugarbeet, cotton, rice, peanut, sunflower and tobacco; pasture and hay crops such as alfalfa, pasture grasses and silage; and fruit and vine crops, such as apples, apricots, cherries, peaches, pears, plums, citrus, grapes, pecans, walnuts, avocados, bananas and kiwis.

In particular embodiments of this invention, the method described herein (having steps (a) through (g)) can further comprise the steps of: h) contacting the supernatant of (g) with magnetic beads in wells of a multiwell plate; i) positioning the multiwell plate on a magnet for a period of time sufficient for nucleic acid present in the supernatant to bind the magnetic beads in the wells of the multiwell plate; j) removing the supernatant from the wells of the multiwell plate; k) washing the magnetic beads with wash buffer [e.g., 50% PA wash buffer (125 mM Tris pH 7.5, 25 mM EDTA, 500 mM NaCl), 25% 2-isopropanol and 25% ethanol (95%)]; l) positioning the multiwell plate on the magnet; m) removing the wash buffer; n) repeating steps (k) and (l) at least two times; o) drying the magnetic beads under conditions whereby the ethanol in the wash buffer evaporates; p) adding elution buffer to the wells of the multiwell plate to elute the nucleic acid from the magnetic beads; q) positioning the multiwell plate on the magnet for a period of time sufficient for the magnetic beads to collect at the bottom of the wells of the multiwell plate; r) optionally removing the elution buffer containing the nucleic acid from the wells of the multiwell plate; and s) contacting the elution buffer containing the nucleic acid with reagents for analysis (e.g., detection and/or quantitation) of the nucleic acid.

In some embodiments, step (r) can be carried out and the elution buffer can be removed from the wells of the multiwell plate containing the magbeads and transferred to another plate or container or vessel for analysis of the nucleic acid in the elution buffer according to methods well known in the art. Alternatively, the elution buffer can remain in the wells of the multiwall plate containing the magbeads for analysis of the nucleic acid in the elution buffer according to methods well known in the art.

In some embodiments of the methods described above, the elution buffer can be water, Promega elution buffer, low TE buffer (1 mM Tris, 0.1 mM EDTA, pH 8.0), or TE buffer (10 mM Tris-Cl, 1 mM EDTA, pH 8.0).

In various embodiments, the reagents for analyzing the nucleic acid are reagents for amplification of nucleic acid, as described herein.

DEFINITIONS

As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The term "plant" is intended to encompass plants at any stage of maturity or development, as well as any tissues or organs (plant parts) taken or derived from any such plant unless otherwise clearly indicated by context. The present invention also includes transgenic seeds produced by the transgenic plants of the present invention. In one embodiment, the seeds are true breeding for an increased resistance to nematode infection as compared to a wild-type variety of the plant seed. In particular embodiments of the invention, the plant is a soybean plant.

As used herein, the term "plant part" includes but is not limited to pollen, seeds, branches, fruit, kernels, ears, cobs, husks, stalks, root tips, anthers, stems, roots, flowers, ovules, stamens, leaves, embryos, meristematic regions, callus tissue, anther cultures, gametophytes, sporophytes, pollen, microspores, protoplasts, hairy root cultures, and the like. plant cells including plant cells that are intact in plants and/or parts of plants, plant protoplasts, plant tissues, plant cell tissue cultures, plant calli, plant clumps, and the like. Further, as used herein, "plant cell" refers to a structural and physiological unit of the plant, which comprises a cell wall and also may refer to a protoplast. Thus, as used herein, a "plant cell" includes, but is not limited to, a protoplast, gamete producing cell, and a cell that regenerates into a whole plant. Tissue culture of various tissues of plants and regeneration of plants therefrom is well known in the art.

A plant cell of the present invention can be in the form of an isolated single cell or can be a cultured cell or can be a part of a higher-organized unit such as, for example, a plant tissue or a plant organ.

Also as used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Nucleic acid sequences provided herein are presented herein in the 5' to 3' direction, from left to right and are represented using the standard code for representing the nucleotide characters as set forth in the U.S. sequence rules, 37 CFR §§1.821-1.825 and the World Intellectual Property Organization (WIPO) Standard ST.25.

A "nucleic acid" or "nucleic acid molecule" is a nucleotide sequence (either DNA or RNA) that is present in a form or setting that is different from that in which it is found in nature and is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. Thus, a nucleic acid molecule found in nature that is removed from its native environment and transformed into a plant is still considered "isolated" even when incorporated into a genome of the resulting transgenic plant. It also includes a recombinant nucleic acid that is part of a hybrid nucleic acid encoding an additional polypeptide or peptide sequence.

The term "isolated" can further refer to a nucleic acid, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid, nucleotide sequence or polypeptide that is not naturally occurring as a fragment and would not be found as such in the natural state. "Isolated" does not mean that the preparation is technically pure (homogeneous), but it is sufficiently pure to provide the polypeptide or nucleic acid in a form in which it can be used for the intended purpose.

In representative embodiments of the invention, an "isolated" nucleic acid, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

The present invention also provides a kit comprising reagents, buffers, diluents, devices and/or instruments, etc., to carry out the methods of this invention. It would be well understood by one of ordinary skill in the art that the kits of this invention can comprise one or more containers and/or receptacles to hold the reagents of the kit, along with appropriate buffers and/or diluents and directions for using the kit, as would be well known in the art.

The following examples are not intended to limit the scope of the claims to the invention, but are rather intended to be exemplary of certain embodiments. Any variations in the exemplified methods that occur to the skilled artisan are intended to fall within the scope of the present invention. As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

EXAMPLES

Example 1

Determination of Feasibility of Extracting Both Protein and DNA from a Single Sample Using a Dual Extraction Method Summary of Results.

Several parameters were tested to optimize protein extraction of maize leaf tissue followed by DNA extraction of the remaining tissue. Seventeen different trait assays were analyzed and both lyophilized and frozen leaf tissue were tested. Logistics of testing large numbers of samples were explored. Processing the samples for both protein and DNA worked well for all of the traits tested. This process worked well on both frozen and lyophilized tissue and can be performed following current high-throughput methods.

Methods.

Newly transformed maize plants were sampled in separate blocks for both secondary TaqMan and ELISA following the standard sampling protocol. The samples in the secondary TaqMan block were processed normally. The samples in the ELISA block were ground using a tissue homogenizer (e.g., Kleco or tissue pulverizer) and extracted for protein by the addition of 0.25 ml PBST (phosphate buffered saline containing 0.05% Tween-20) followed by manual shaking of the block. The block was spun for 5 min at 4000 rpm and 0.2 ml of the supernatant containing nondenatured proteins was transferred to another block for subsequent ELISA processing and testing.

On the pellet, a modified DNA extraction procedure was performed. DNA lysis buffer (0.2 ml) was added and the block was shaken on the tissue homogenizer for 10 sec and then spun for 10 min. This supernatant containing the DNA was then processed according to a DNA isolation procedure using magbeads. Briefly, 0.1 ml of the supernatant is transferred to a 96-well plate (e.g., multiwall plate) containing 5 µl per well of magbeads. The multiwell plate is positioned on a magnet for a period of time sufficient for nucleic acid present in the supernatant to bind the magnetic beads in the wells of the multiwell plate. The supernatant fluid is removed from the wells of the multiwell plate and the magnetic beads are washed with wash buffer [e.g., 50% PA wash buffer (125 mM Tris pH 7.5, 25 mM EDTA, 500 mM NaCl), 25% isopropanol and 25% ethanol (95%)]. The multiwall plate is again positioned on the magnet and wash buffer is removed. The washing and positioning steps are repeated at least two times. The magnetic beads are then dried under conditions whereby the ethanol in the wash buffer evaporates. Elution buffer [non-limiting examples of which include water, Promega elution buffer, low TE buffer (1 mM Tris, 0.1 mM EDTA, pH 8.0), TE buffer (10 mM Tris, 1 mM EDTA, pH 8.0)] is then added to the wells of the multiwell plate to elute the nucleic acid from the magnetic beads. The multiwall plate is positioned on the magnet for a period of time sufficient for the magnetic beads to collect at the bottom of the wells of the multiwell plate. The elution buffer containing the nucleic acid can be removed from the wells of the multiwell plate for further analysis of the nucleic acid and/or the elution buffer containing the nucleic acid can remain in the wells of the multiwall plate and be contacted directly with reagents (e.g., reagents for amplification of nucleic acid) for further analysis of the nucleic acid.

Results.

Criteria used for determining best conditions included that the endogenous gene (TET) cycling time (Ct) value had to be within range (22-26) and 0.2 ml of protein extract with sufficient total protein was needed for ELISA testing. Optimum leaf tissue size was determined to be 4 leaf discs and the best protein extraction buffer was PBST.

Several samples were analyzed following the dual extraction method and compared to the results from samples extracted by a standard TaqMan DNA extraction method (e.g., Promega DNA extraction kit). No significant difference in the results was seen between the two extraction methods. Seventeen different TaqMan assays were used for this comparison over a 4 month testing period.

Additional testing was performed on a large field sample data set to explore the logistics of testing large numbers of samples. Existing instrumentation was used to process these samples following minimum changes to current high thoughput processes. No difference was seen in data quality between samples sitting in protein extraction buffer from 15 min to 165 min before the addition of DNA lysis buffer or in samples sitting in DNA extraction buffer for up to 24 hr before processing. Also, greater than 99% of the samples recovered sufficient DNA to obtain a quality result.

This method would reduce the amount of sampling from 5 blocks to 2 blocks (40% reduction) as well as lower the cost of consumables.

Conclusions.

A dual extraction method was developed that allowed the isolation of both protein and DNA from a single plant tissue sample. The protein was extracted first in order to isolate the protein in its native form (non-denatured), followed by extraction of DNA from what remained of the single tissue sample. The results from this dual extraction method are comparable to the standard DNA extraction method results and ELISA results. Large numbers of samples were processed utilizing existing high through-put processes without affecting protein or DNA results. Implementing this dual extraction process could potentially reduce cost of analysis by 40-50%.

Example 2

Protein/DNA Dual Extraction

Comparison of Dual Protein/DNA Extraction to a Standard DNA Extraction.

Maize leaf tissue from 8 different plants was sampled in duplicate in 2 separate deep 96-well blocks. One block was processed by a standard DNA extraction method and the other block was extracted first for protein followed by the same standard DNA extraction method. The DNA recovered from both extractions was tested for two genes using real time PCR (polymerase chain reaction) TaqMan technology, which can measure the number of copies of a specific gene. The average Ct value of the endogenous gene (TET) was compared for each gene measured and was within the 22-26 acceptable range for both DNA extraction methods. The Ct value indicated that the quantity of the DNA extracted was sufficient to obtain good results. Copy calls can be determined by the groupings in the scatter plots. Tightness of the groupings can be used as an indicator of the quality. The number of copies determined from the DNA extracted using the dual extraction method is identical to the number of copies determined from the standard DNA extraction method. Extracting protein first before isolating the DNA does not affect the outcome of the real time PCR results.

Quality of DNA from the Dual Extraction Method.

To evaluate the quality of DNA obtained from the dual extraction method and the robustness of this method, over 2500 maize leaf samples were tested in 17 different real time PCR (TaqMan) assays. Number of copies of each gene, average Ct value and DNA concentration were compared. The average TET Ct value for the dual extraction method matched the corresponding standard DNA extraction method. Also, copy call matches between the two processes averaged greater than 93%. Average DNA concentrations recovered, as measured by Pico green, were very similar, indicating that extracting protein first does not prevent good DNA recovery.

Testing Process in a High-Throughput Format.

Over 2400 lyophilized maize leaf samples were tested using the dual protein/DNA extraction method. The protein extract was tested by ELISA and the extracted DNA was tested in 3 different TaqMan assays. Automation processes were employed in order to process this number of samples. During the processing, samples were in protein extraction buffer for 15 to 165 min before the addition of DNA lysis buffer to begin the DNA extraction. Greater than 98% of the samples were in agreement between the protein ELISA results and the DNA TaqMan results. Less than 1% of the samples resulted in a poor DNA extraction with no results obtained. The results also show that the DNA in plant tissue extracted in protein extraction buffer is stable for at least 2.5 hours. No difference in average TET Ct value was seen between samples which remained in protein extraction buffer for 15 minutes vs. 165 minutes.

Example 3

Stability Studies

Stability of the leaf extract in the protein extraction buffer or the DNA lysis buffer was evaluated. Samples were incubated in PBST, pellet without PBST, or DNA lysis buffer for up to 3 days at room temperature or at 4° C. before extracting the DNA. For ELISA testing, most of the proteins tested are stable for up to 72 hrs at 4° C. in PBST. Both lyophilized tissue and fresh tissue stability were equivalent. Room temperature storage showed more degradation over time and is not recommended for storing the extracts.

For DNA stability, DNA was extracted from the tissue from each of the 3 storage conditions described above (in PBST, pellet without PBST, or DNA lysis buffer). DNA stability was evaluated by analyzing both the median endogenous cycle value (median TET Ct) and standard deviation of the samples. These two measures will give an indication of DNA quality and will determine the accuracy of the copy call. Thus as DNA stability/quality decreases, copy calls will be affected. DNA in extracts stored at 4° C. in PBST or without PBST were stable, with good TET Ct values and low standard deviations for both fresh and lyophilized tissue. Extracts stored in lysis buffer had higher standard deviations at 24 hrs, indicating a decrease in DNA quality. Room temperature storage experiments also had higher standard deviations.

Results of the stability testing indicate that extracts can be prepared and can be stored at 4° C. with or without the PBST removed for up to 24 hrs without loss of protein and without DNA degradation. Storage in lysis buffer is not recommended.

Example 4

Dual Extraction Method Using Sugarcane Leaf Tissue

Sugarcane leaf tissue was sampled in duplicate in 2 separate deep 96-well blocks. Samples in one block were processed by the standard DNA extraction method described herein and the samples in the other block were processed by the dual extraction method described herein, in which protein was extracted first from the sample and DNA was extracted from what remained of the sample according to the DNA extraction method described herein. The DNA recovered from both extractions was tested for six different genes using real time PCR (polymerase chain reaction) TaqMan technology. Table X shows the results of this experiment. The average TET Ct value for the dual extraction method matched the corresponding standard DNA extraction method for all genes tested. Also, copy call matches averaged 93% between the 2 processes. Amplification plots show the similarity of the endogenous amplification between the samples processed by the dual extraction method or the DNA extraction method described herein. These results indicate that sugarcane leaf tissue can be extracted first for protein before isolating the DNA. This dual extraction process does not affect the outcome of the real time PCR results.

All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the list of the foregoing embodiments and the appended claims.

What is claimed is:

1. A method of isolating nucleic acid and undenatured and unreduced protein from the same biological sample, comprising, in the following order:
   a) disrupting the biological sample, which comprises protein that is not denatured and not reduced;
   b) contacting the disrupted biological sample of (a) with a protein lysis buffer that lacks any component that denatures or reduces protein to produce a first lysate;
   c) centrifuging the first lysate of (b) to produce a first supernatant containing undenatured and unreduced protein and a pellet containing nucleic acid;
   d) removing the first supernatant of (c), thereby isolating undenatured and unreduced protein from the biological sample;
   e) contacting the pellet of (d) with nucleic acid lysis buffer to produce a second lysate;
   f) centrifuging the second lysate of (e) to produce a second supernatant containing nucleic acid; and
   g) removing the second supernatant of (f), thereby isolating nucleic acid from the same biological sample.

2. The method of claim 1, wherein the protein lysis buffer of (b) is Protein Lysis Buffer A (phosphate buffered saline with 0.05% Tween-20) or BB-PVP-Tw buffer [borate buffer 0.1M, pH 7.5, 0.2% polyvinylpyrrolidone (PVP), 0.5% Tween-20].

3. The method of claim 1, wherein the protein lysis buffer of (b) lacks sodium dodecyl sulfate (SDS), urea, guanidine, 2-mercaptoethanol and dithiothreitol.

4. The method of claim 1, wherein the nucleic acid lysis buffer of (e) is PA lysis buffer (4M guanidine thiocyanate, 10 mM Tris, pH 7.5).

5. The method of claim 1, further comprising the step of detecting protein in the first supernatant of (d) by ELISA.

6. The method of claim 1, further comprising the step of analyzing the nucleic acid in the second supernatant of (g) by an amplification reaction.

7. The method of claim 6, wherein the amplification reaction is a polymerase chain reaction (PCR).

8. The method of claim 1, wherein the biological sample is from a plant.

9. The method of claim 8, wherein the biological sample is leaf tissue from the plant.

10. The method of claim 8, wherein the plant is corn, soy, sugarcane or wheat.

11. The method of claim 1, carried out in a high throughput format.

* * * * *